United States Patent
Sato (10) Patent No.: US 9,713,823 B2
(45) Date of Patent: Jul. 25, 2017

(54) CONTINUOUS GALVANIZING LINE HAVING AN ANNEALING FURNACE

(71) Applicant: JFE STEEL CORPORATION, Chiyoda-ku, Tokyo (JP)

(72) Inventor: Nobuyuki Sato, Chiba (JP)

(73) Assignee: JFE STEEL CORPORATION, Tokyo (JP)

( * ) Notice: Subject to any disclaimer, the term of this patent is extended or adjusted under 35 U.S.C. 154(b) by 0 days.

(21) Appl. No.: 14/390,648

(22) PCT Filed: Feb. 27, 2013

(86) PCT No.: PCT/JP2013/001156
§ 371 (c)(1),
(2) Date: Oct. 3, 2014

(87) PCT Pub. No.: WO2013/150710
PCT Pub. Date: Oct. 10, 2013

(65) Prior Publication Data
US 2015/0090182 A1 Apr. 2, 2015

(30) Foreign Application Priority Data

Apr. 6, 2012 (JP) .................................. 2012-087313

(51) Int. Cl.
*B05C 3/00* (2006.01)
*B05C 11/10* (2006.01)
(Continued)

(52) U.S. Cl.
CPC ............ *B05C 11/1015* (2013.01); *C21D 1/76* (2013.01); *C21D 8/0473* (2013.01); *C21D 9/561* (2013.01);
(Continued)

(58) Field of Classification Search
CPC .. C21D 1/76; C21D 1/26; F27B 9/068; F27D 7/06; C23C 2/28; C23C 2/40; C23C 2/06; C23C 14/544
See application file for complete search history.

(56) References Cited

U.S. PATENT DOCUMENTS 4,632,706 A * 12/1986 Mueller .................... C23G 5/04
134/3
4,676,999 A * 6/1987 Furukawa .............. C21D 9/561
118/718
(Continued)

FOREIGN PATENT DOCUMENTS

EP 1936000 6/2008
EP 2407572 1/2012
(Continued)

OTHER PUBLICATIONS

International Search Report dated Apr. 9, 2013, application No. PCT/JP2013/001156.
(Continued)

*Primary Examiner* — Karl Kurple
(74) *Attorney, Agent, or Firm* — RatnerPrestia (57) ABSTRACT

A continuous galvanizing line having an annealing furnace of an all radiant tube heating type includes a moisture removal device, dew-point meters, outlets through which the atmospheric gas in the furnace is collected and inlets through which the atmospheric gas from which moisture has been removed with the moisture removal device is fed into the furnace, the dew-point meters and the outlets being placed at least at two points which respectively exist on a side wall in the vicinity of the entrance of the annealing furnace and on a side wall in the vicinity of the furnace top or the furnace bottom at a position where a steel sheet has a maximum end-point temperature, the inlets being placed at two points which respectively exist on side walls on the
(Continued)

sides opposite to the sides of the two points for the outlets in the height direction of the furnace, making it possible to steadily control the dew-point of the atmospheric gas to be −45° C. or lower and −80° C. or higher throughout the whole area of the annealing furnace.

8 Claims, 2 Drawing Sheets

(51) Int. Cl.
| | | |
|---|---|---|
| *C21D 1/76* | (2006.01) | |
| *C23C 2/00* | (2006.01) | |
| *C23C 2/40* | (2006.01) | |
| *C23C 2/06* | (2006.01) | |
| *C21D 8/04* | (2006.01) | |
| *C21D 9/56* | (2006.01) | |
| *C23C 2/02* | (2006.01) | |
| *F27D 99/00* | (2010.01) | |
| *F27B 9/28* | (2006.01) | |
| *F27D 7/06* | (2006.01) | |
| *G01N 25/66* | (2006.01) | |

(52) U.S. Cl.
CPC .............. *C23C 2/003* (2013.01); *C23C 2/02* (2013.01); *C23C 2/06* (2013.01); *C23C 2/40* (2013.01); *F27B 9/28* (2013.01); *F27D 7/06* (2013.01); *F27D 99/0001* (2013.01); *F27D 2007/063* (2013.01); *G01N 25/66* (2013.01)

(56) References Cited

U.S. PATENT DOCUMENTS

| | | | | | |
|---|---|---|---|---|---|
| 6,030,714 | A * | 2/2000 | Fujibayashi | .......... | C22C 38/002 148/276 |
| 6,053,430 | A * | 4/2000 | Wu | .......... | F23D 14/22 239/423 |
| 6,224,692 | B1 * | 5/2001 | Cantacuzene | .......... | C23C 2/02 148/533 |
| 6,228,321 | B1 * | 5/2001 | Umetsu | .......... | C21D 1/76 148/582 |
| 7,384,489 | B2 * | 6/2008 | Raick | .......... | C21D 1/76 148/634 |
| 8,752,502 | B2 * | 6/2014 | Eriksson | .......... | C23C 2/003 118/419 |
| 9,222,146 | B2 * | 12/2015 | Sato | .......... | C23C 2/003 |
| 2007/0051438 | A1 * | 3/2007 | Honda | .......... | C21D 1/76 148/533 |
| 2009/0123651 | A1 * | 5/2009 | Okada | .......... | C23C 2/28 427/319 |
| 2010/0173072 | A1 * | 7/2010 | Borrel | .......... | C21D 1/76 427/248.1 |
| 2012/0180721 | A1 * | 7/2012 | Hoshino | .......... | C21D 9/56 118/708 |
| 2014/0178567 | A1 * | 6/2014 | Lyons | .......... | B05D 1/60 427/8 |
| 2015/0013851 | A1 * | 1/2015 | Takahashi | .......... | C23C 2/02 148/508 |
| 2015/0140217 | A1 * | 5/2015 | Takahashi | .......... | C21D 1/74 427/321 |
| 2015/0140218 | A1 * | 5/2015 | Takahashi | .......... | C23C 2/02 427/321 |
| 2015/0159235 | A1 * | 6/2015 | Takahashi | .......... | C21D 1/76 148/533 |
| 2015/0225829 | A1 * | 8/2015 | Fujita | .......... | C23C 2/40 428/659 |

FOREIGN PATENT DOCUMENTS

| | | |
|---|---|---|
| EP | 2623629 A1 | 8/2013 |
| JP | 55-122865 | 9/1980 |
| JP | H 04-116127 A | 4/1992 |
| JP | H 05-271891 A | 10/1993 |
| JP | 7-138652 A | 5/1995 |
| JP | 11-236623 A | 8/1999 |
| JP | 00219949 A | 8/2000 |
| JP | 2000219949 A | 8/2000 |
| JP | 03129125 A | 5/2003 |
| JP | 2003129125 A | 5/2003 |
| JP | 2005060743 | 3/2005 |
| JP | 2010-255100 A | 11/2010 |
| KR | 20080046241 | 5/2008 |
| WO | WO2012043863 A1 | 4/2012 |
| WO | WO 2012/081719 A1 | 6/2012 |

OTHER PUBLICATIONS

Korean Notice of Allowance with English transiation for Application No. 10-2014-7028129, dated Jun. 10, 2016, 2 pages.

Extended European Search Report mailed Mar. 31, 2015 in European Application No. 13772451.4.

Chinese Office Action of 201380017076.9 issued Apr. 5, 2016 with Japanese translation and English language concise statement of relevance.

* cited by examiner

CONTINUOUS GALVANIZING LINE HAVING AN ANNEALING FURNACE

CROSS REFERENCE TO RELATED APPLICATIONS

This is the U.S. National Phase application of PCT/JP2013/001156, filed Feb. 27, 2013, which claims priority to Japanese Patent Application No. 2012-087313, filed Apr. 6, 2012, the disclosures of each of these applications being incorporated herein by reference in their entireties for all purposes.

FIELD OF THE INVENTION

The present invention relates to a continuous galvanizing line and, specifically, a continuous galvanizing line consisting of an annealing furnace of an all radiant tube heating type which can be ideally used for manufacturing a galvanized steel sheet and a galvannealed steel sheet having excellent zinc coatability.

BACKGROUND OF THE INVENTION

Nowadays, in the fields of, for example, automobiles, home electrical appliances and building material industries, surface treated steel sheets which are manufactured by providing untreated steel sheets with corrosion resistance, in particular, galvanized steel sheets and galvannealed steel sheets (hereinafter, generically called "galvanized steel sheets"), are widely used. In addition, from the viewpoint of the improvement of fuel efficiency and collision safety, the application of high strength steel sheets to automobile bodies has been progressing in order to decrease the weight and increase the strength of the automobile bodies by decreasing the thickness of car body materials by increasing the strength of the materials.

The galvanized steel sheet described above is manufactured from a thin steel sheet, which is manufactured by hot-rolling a steel material and then by cold-rolling the hot-rolled steel sheet, by performing recrystallization annealing on the thin steel sheet in an annealing furnace constituting a part of a continuous galvanizing line, and then by performing a hot dip galvanizing treatment on the steel sheet, or optionally, by further performing a galvannealing on the galvanized steel sheet.

Although examples of heating methods of the annealing furnace constituting a part of a continuous galvanizing line include a DFF type (direct fire furnace type), an NOF type (non-oxidation furnace type) and an all radiant tube type, recently, the number of the lines consisting of an annealing furnace of an all radiant tube heating type has been increasing for the reasons of, for example, easy operation, low possibility of occurrence of pick up and low cost at which a coated steel sheet of high quality can be manufactured.

On the other hand, as an example of a method for increasing the strength of a galvanized steel sheet, a method in which a large amount of chemical elements such as Si and Mn which are effective for strengthening steel is contained in steel for the purpose of solid solution strengthening is widely used. However, there is a problem in that, since the chemical elements described above such as Si and Mn are elements which are easily oxidized, these chemical elements markedly decrease the wettability of hot dip zinc coating (zinc coatability). In view of this, in a conventional furnace of a DFF type and an NOF type, zinc coatability is improved by forming an internal oxidation layer inside the steel sheet by positively oxidizing the surface of the steel sheet in a heating furnace in order to form an oxidized film which mainly contains Fe while the concentration of the chemical elements such as Si and Mn at the surface of the steel sheet is suppressed, by reducing the surface in a reducing atmosphere, and by performing a coating treatment (refer to Patent Literature 1). However, there is a problem in that, since it is impossible to include an oxidation process in an annealing furnace of an all radiant tube heating type, it is impossible to achieve good zinc coatability of a steel sheet which contains chemical elements such as Si and Mn.

As an example of a method for solving the problem described above, Patent Literature 2 discloses a method in which a high strength galvanized steel sheet which contains a large amount of the chemical elements such as Si and Mn is manufactured by suppressing the internal oxidation of the surface layer of the steel sheet by controlling the dew-point of the atmosphere at a temperature in the range of 600° C. or higher in an annealing furnace to −40° C. or lower. However, although it is disclosed that a dew-point is controlled to −40° C. or lower in this method and that a specific method for achieving the specified dew-point is to absorb and remove the moisture in the furnace with an absorbent, it is difficult to steadily keep the dew-point of an atmospheric gas in the furnace at −40° C. or lower. Therefore, there is a problem in that it is impossible to steadily manufacture a high strength galvanized steel sheet having excellent zinc coatability by only using the method disclosed in Patent Literature 2.

Incidentally, as an example of a method for controlling the dew-point temperature of an atmospheric gas in a furnace, Patent Literature 3 discloses an annealing furnace, in which thin metal strips which are continuously fed into the furnace are directly heated and cooled in a reducing atmosphere, the furnace consisting of a circulation system in which the gas in the furnace is discharged to the outside of the furnace through a ventilation pipe which is placed at the boundary of an interior refractory and an exterior steel shell of the furnace wall, then the discharged gas is cleaned by removing moisture and oxygen from the gas, and then the cleaned gas is returned to the furnace. However, since the object of this method is to reduce the time required to start up a bright annealing furnace for stainless steel at the beginning of its operation or at the resumption of its operation after repair, there is no mention of the improvement of the zinc coatability of the surface of a steel sheet. In addition, gas discharged from the inside of the furnace and the inlet side and outlet side of the furnace is fed into a cooling zone after the impurities of the gas have been removed but not directly into the furnace. Moreover, the atmospheric gas is not discharged from the inside of the furnace after the refractory has been dried (during operation). Furthermore, although the dew-point temperature of the discharged gas is observed, the dew-point temperature of the inside of the furnace is not observed. Therefore, the distribution of the dew-point temperature is left unknown.

In addition, Patent Literature 4 discloses a method for manufacturing a high strength galvanized steel sheet having Si content of from 0.2 mass % to 2.0 mass % by using a continuous galvanizing line consisting of a non-oxidation furnace, the method including controlling the thickness of an oxidized film on the surface of the steel sheet by adjusting the combustion air ratio of the non-oxidation furnace and the dew-point of the atmosphere of a reducing furnace in order to improve zinc coatability. However, although it is disclosed that a dew-point is controlled in this method, this is a method for improving zinc coatability by using oxidationreduction reaction in the non-oxidation furnace and the reducing furnace, which means that this is not a method which can be applied to a furnace of an all radiant tube heating type in which the surface of a steel sheet is not positively reduced.

In addition, Patent Literature 5 discloses an annealing line of a reducing atmosphere for a metal strip, the line consisting of a circulating channel which consists of a refining device through which an atmospheric gas is circulated and in which moisture is adsorbed. However, the object of the refining device of this annealing line is to prevent defective coloring of the surface of the metal strip which occurs when the thickness of the strip is switched between thin and thick gauges, and not to improve zinc coatability. Moreover, the control of dew-point is not investigated.

PATENT LITERATURE

[PTL 1] Japanese Unexamined Patent Application Publication No. 55-122865
[PTL 2] Japanese Unexamined Patent Application Publication No. 2010-255100
[PTL 3] Japanese Unexamined Patent Application Publication No. 04-116127
[PTL 4] Japanese Unexamined Patent Application Publication No. 05-271891
[PTL 5] Japanese Unexamined Patent Application Publication No. 11-236623

SUMMARY OF THE INVENTION

The present invention has been completed in view of the problems which the conventional methods have, and an object of the present invention is to provide a continuous galvanizing line with which a galvanized steel sheet having excellent zinc coatability can be steadily manufactured by preventing the oxidation of the surface of the steel sheet with certainty in an annealing furnace.

The present inventors diligently conducted investigations in order to solve the problems described above, and, as a result, found that it is not sufficient only to control the dew-point of an atmospheric gas to be −40° C. or lower at a temperature of 600° C. or higher in an annealing furnace and that it is necessary to control the dew-point of the atmospheric gas to be between −80° C. and −45° C. everywhere from the entrance to the exit of the annealing furnace, which led to the completion of the present invention.

That is to say, an embodiment of the present invention includes a continuous galvanizing having an annealing furnace of an all radiant tube heating type, the line has a moisture removal device with which an atmospheric gas in the annealing furnace is collected and moisture is removed from the gas and then the gas is returned to the furnace; dew-point meters, with which the dew-point of the atmospheric gas is observed, and the outlets, through which the atmospheric gas in the furnace is collected, being placed at least at two points which respectively exist on a side wall in the vicinity of the entrance of the annealing furnace and on a side wall in the vicinity of the furnace top or the furnace bottom at the position where a steel sheet has a maximum end-point temperature; and inlets, through which the atmospheric gas from which moisture has been removed with the moisture removal device is fed into the furnace, being placed at two points which respectively exist on side walls opposite to said two points in the height direction of the furnace; and thereby, making it possible to steadily control the dew-point of the atmospheric gas to be between −80° C. and −45° C. throughout the whole area of the annealing furnace.

The continuous galvanizing line according to an embodiment of the present invention, the line in addition said two points further has a dew-point meter, with which the dew-point of the atmospheric gas is observed, being placed on a side wall at a central position in the height direction of the furnace at a position nearest to the entrance of the furnace in the length direction of the furnace within the area in which the temperature of the steel sheet becomes 600° C.; and an inlet, through which the atmospheric gas from which moisture has been removed with the moisture removal device is fed into the furnace, being placed on the side wall in the vicinity of the furnace top or the furnace bottom at the position in the length direction of the furnace where the dew-point meter is placed.

In addition, the continuous galvanizing line according to an embodiment of the present invention is characterized in that the flow rate and/or the dew-point of the atmospheric gas which is fed through each inlet described above can be separately adjusted in accordance with the dew-point which is observed with the dew-point meter nearest to the inlet.

In addition, the continuous galvanizing line according to an embodiment of the present invention is characterized in that the line makes it possible to steadily control the dew-point of the atmospheric gas to be between −80° C. and −50° C. throughout the whole area of the annealing furnace.

According to an embodiment of the present invention, since it is possible to steadily control the dew-point of the atmospheric gas to be −45° C. or lower throughout the whole area in the furnace, it is possible to prevent the oxidation of the surface of a steel sheet with certainty when annealing is performed, which makes it possible to steadily provide a galvanized steel sheet having excellent zinc coatability.

DETAILED DESCRIPTION OF EMBODIMENTS OF THE INVENTION

Figure 1:
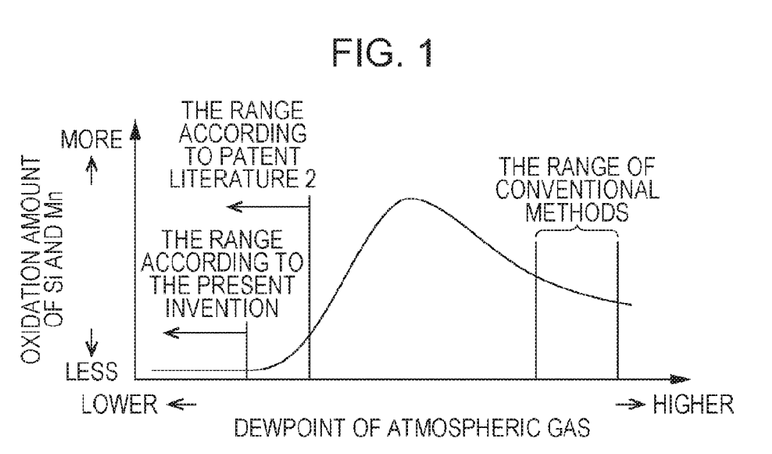
FIG. 1 is a diagram illustrating the influence of the dew-point of an atmospheric gas on oxidation amount.

FIG. 1 schematically illustrates the influence of the dew-point of an atmospheric gas on the oxidation amount of the surface of a steel sheet when the steel sheet is subjected to annealing at a temperature of 600° C. or higher. Although the oxidation amount of the surface of the steel sheet increases with an increase in the dew-point of the atmospheric gas, the diffusion of chemical elements such as Si and Mn is suppressed because of the formation of an oxidized layer inside the surface layer of the steel sheet after the oxidation amount has increased to some extent, which results in the formation of an oxidation layer which mainly contains Fe. Therefore, in the conventional method according to, for example, Patent Literature 1, good zinc coatability is achieved by reducing the oxidation layer which mainly contains Fe. That is to say, the dew-point of the atmospheric gas in the conventional method is set on the side of the higher dew-point in FIG. 1.

However, in the case of a galvanizing line which consists of an annealing furnace of an all radiant tube heating type, since there is no oxidation process, it is impossible to improve zinc coatability by using the method described above. Therefore, in the method according to Patent Literature 2, contrary to the conventional method, as illustrated on the left hand side of FIG. 1, it is intended to improve zinc coatability by suppressing the formation of an oxidation film as much as possible through removal of moisture in the atmospheric gas with an absorbent and setting the dew-point of the atmospheric gas to be −40° C. or lower in an area of the furnace where the temperature is 600° C. or higher.

The dew-point of the atmospheric gas depends on the moisture content of the atmospheric gas. The moisture consists of, other than the moisture released from the refractory and the fire-resistant material of the inner wall of the annealing furnace, the moisture contained in the air which comes in through the entrance of the annealing furnace and the moisture which is adsorbed on the surface of a steel sheet and brought into the furnace. The former moisture content which is released from the inner wall of the furnace is brought into the furnace when the furnace is opened on the occasion of periodic maintenance and the like and decreases over time of operation. On the other hand, the moisture content which is brought through the entrance of the annealing furnace widely varies depending on the material to be treated and operational conditions. Therefore, there is a case where there is a negative effect on the dew-point of the atmospheric gas not only in the vicinity of the entrance of the annealing furnace but also in the area of the furnace where the temperature of the steel sheet becomes high and the oxidation of the steel sheet is promoted.

Figure 2:
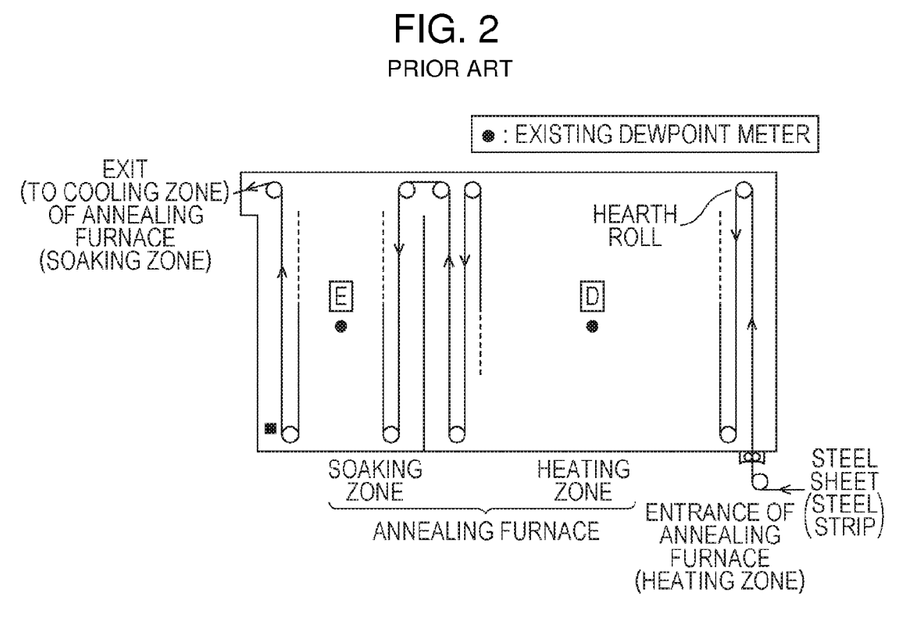
FIG. 2 is a schematic diagram illustrating an annealing furnace constituting a conventional continuous galvanizing line.

However, in the case of a conventional annealing furnace, for example, in the case of an annealing furnace consisting of a heating zone and a soaking zone (hereinafter, the meaning of the word "an annealing furnace" includes a heating zone and a soaking zone), the dew-point of the atmospheric gas is observed, as illustrated in FIG. 2, only with dew-point meters which are respectively placed in the vicinity of the central position of the heating zone and in the vicinity of the soaking zone (points D and E in FIG. 2). Moreover, in the investigations conducted by the present inventors, it has been clarified that it is necessary to control the dew-point of the atmospheric gas to be −45° C. or lower in order to almost completely prevent the oxidation of Mn and Si on the surface of a steel sheet when the temperature of the steel sheet is 600° C. or higher.

Therefore, it is not sufficient to control the dew-point of the atmospheric gas to be −40° C. or lower in an area of the furnace where the temperature is 600° C. or higher as in the method according to Patent Literature 2, and, moreover, it is impossible to maintain the dew-point of the atmospheric gas at −40° C. or lower with certainty when the variation of the dew-point occurs as described above. Therefore, coating defects such as defective adhesion of a coated film occasionally occur.

Therefore, the present invention makes it is possible to control the dew-point of an atmospheric gas to be −45° C. or lower with certainty throughout the whole area of an annealing furnace, by installing a moisture removal device (refiner) in the annealing furnace as an incidental facility, by achieving a low dew-point by removing moisture from the atmospheric gas having a high dew-point which has been collected from the inside of the furnace with the moisture removal device, and then by returning the gas to the inside of the annealing furnace.

Figure 3:
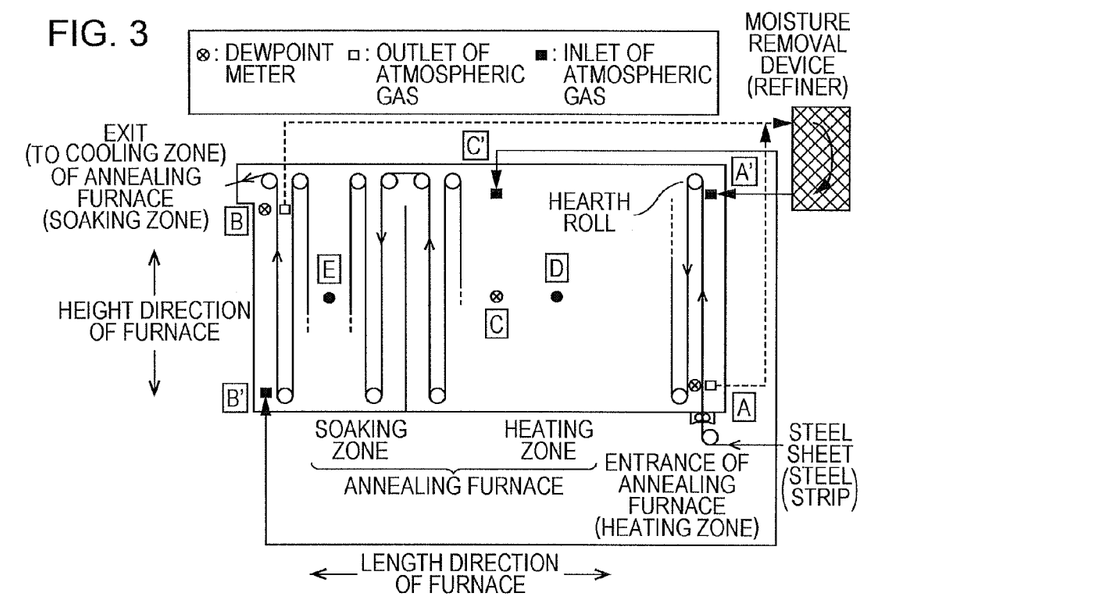
FIG. 3 is a schematic diagram illustrating an annealing furnace constituting the continuous galvanizing line according to an embodiment of the present invention.

Specifically, the continuous galvanizing line according to an embodiment of the present invention, as FIG. 3 illustrates, consists of at least one moisture removal device in an annealing furnace, dew-point meters with which the dew-point of the atmospheric gas is observed, outlets through which the atmospheric gas in the furnace is collected and carried to the moisture removal device and inlets through which the atmospheric gas from which moisture has been removed with the moisture removal device is fed into the furnace, the dew-point meters and the outlets being placed at least at two points which respectively exist on the side wall in the vicinity of the entrance of the annealing furnace (point A in FIG. 3) and on the side wall in the vicinity of the furnace top or the furnace bottom at the position where a steel sheet has a maximum end-point temperature (point B in FIG. 3 (an example of the furnace top)), the inlets being placed at two points which respectively exist on the side walls on the sides opposite to the sides of the two points for the outlets in the height direction of the furnace (points A' and B' in FIG. 3).

Here, the reason why the dew-point meter and the outlet of the atmospheric gas are placed at the position in the annealing furnace where the steel sheet has a maximum end-point temperature (point B in FIG. 3) is that, since the oxidation of the surface of the steel sheet is severer at a higher temperature, it is necessary to make the dew-point −45° C. or lower with certainty at the position where the steel sheet has a maximum end-point temperature and that, in the case where the dew-point of the atmospheric gas which is observed with the dew-point meter is high, it is necessary to quickly collect the atmospheric gas and to quickly feed the atmospheric gas of a low dew-point which is fed to the inside of the furnace through the inlets described below to the position where the steel sheet has a maximum end-point temperature.

Incidentally, it is usual that there is the position described above where the steel sheet has a maximum end-point temperature in the vicinity of the exit of a soaking zone where the steel sheet passes immediately before moving from the soaking zone to a cooling zone. Therefore, although it is preferable that the dew-point meter and the outlet be placed at point B in FIG. 3 in the case where there is the exit of the soaking zone is on the furnace top side in the height direction of the furnace as illustrated in FIG. 3 and, to the contrary, that the dew-point meter and the outlet be placed at point B' in FIG. 3 in the case where there is the exit of the soaking zone is on the furnace bottom side in the height direction of the furnace, the arrangement may be reversed.

In addition, the reason why the dew-point meter and the outlet of the atmospheric gas are placed in the vicinity of the entrance of the annealing furnace (point A in FIG. 3) will be described hereafter. That is to say, 1) since it is impossible to completely prevent air of a high dew-point from coming through the entrance of the annealing furnace and the dew-point of the atmospheric gas in the vicinity of the entrance of the annealing furnace inevitably becomes high due to, for example, moisture which is adsorbed on the surface of a steel sheet being carried into the furnace with the steel sheet, it is necessary to prevent the diffusion of moisture into the other areas in the furnace by quickly collecting these gases. In addition, 2) it is difficult to steadily control the dew-point of the atmospheric gas to be −45° C. or lower at the position described above where the steel sheet has a maximum end-point temperature, unless the dew-point of the atmospheric gas starts being controlled to be −45° C. or lower at the entrance of the annealing furnace.

In addition, the reason why the inlets through which the atmospheric gas from which moisture has been removed with the moisture removal device is fed into the furnace are placed at the two points which respectively exist on the side walls on the sides opposite to the sides of the two points at which the dew-point meters and the outlets of the atmospheric gas are placed in the height direction of the furnace (points A' and B' in FIG. 3) is that there is concern that the fed atmospheric gas of a low dew-point is directly discharged in the case where the inlets are placed in the vicinity of the outlets and that it is necessary to make the dew-point of the atmospheric gas throughout the whole area of the inside of the furnace low by preventing the atmospheric gas from stagnating through use of the flow of the atmospheric gas in the furnace which is formed by feeding the atmospheric gas from the side opposite to the side on which the outlet is placed.

Incidentally, since the oxidation of the surface of the steel sheet markedly progresses in the case where the temperature of the steel sheet is 600° C. or higher, it is necessary to strictly control, in particular, the dew-point of the atmosphere of a temperature in this range. However, since an annealing cycle, in particular, the cycle of an annealing temperature, is changed in accordance with the steel grade (chemical composition) of the steel sheet and the mechanical properties which are required of a product sheet, the area in the furnace in which the temperature of the steel sheet becomes 600° C. or higher is also changed. Therefore, according to the present invention, it is preferable that the following method be used in order to control the dew-point of the atmospheric gas to be −45° C. or lower with certainty at the position where the temperature of the steel sheet becomes 60.0° C. or higher. That is to say, a dew-point meter is placed on the side wall at the central position in the height direction of the furnace of the position nearest to the entrance of the furnace in the length direction of the furnace within the area in which the temperature of the steel sheet becomes 600° C. (point C in FIG. 3), an inlet of the atmospheric gas is placed on the side wall in the vicinity of the furnace top or the furnace bottom at a the position 0.5 m or more and 5 m or less from the dew-point meter described above, at the position in the length direction of the furnace where the dew-point meter described above is placed (point C' in FIG. 3), and the flow rate of the atmospheric gas which has been made to have a low dew-point with the moisture removal device is adjusted in accordance with the dew-point which is observed with the dew-point meter. By this method, it is possible to control the dew-point of the atmosphere in the furnace to be −45° C. or lower with certainty in the area of the furnace where the temperature of the steel sheet becomes 600° C. or higher.

Incidentally, it is preferable that a moisture removal device installed in the annealing furnace according to the present invention be able to make the dew-point of the atmospheric gas from which moisture has been removed −60° C. or lower in order to make the dew-point throughout the whole area of the annealing furnace −45° C. or lower. It is difficult to make the dew-point of the atmospheric gas in the furnace −45° C. or lower in the case where the dew-point of the gas from which moisture has been removed is higher than −60° C. In addition, although FIG. 3 illustrates an example in which one moisture removal device is installed, plural moisture removal devices may be installed.

In addition, it is preferable that the flow rate and/or dew-point temperature of the atmospheric gas which is fed through the each of the inlets placed at points A', B' and C' in FIG. 3 be separately controlled in accordance with the dew-point which is observed with the each of the dew-point meters placed at points A, B and C which is nearest to the each of the inlets corresponding to points A', B' and C'. For example, it is preferable that the flow rate of the atmospheric gas which is fed through the each inlet be separately adjusted in the case where one moisture removal device is installed and that the flow rate and/or the dew-point of the atmospheric gas which is fed through the each inlet be separately adjusted in the case where plural moisture removal deices are installed, so that the dew-point temperature of the atmospheric gas at the position where the each dew-point meter is placed can be controlled to be −45° C. or lower. Incidentally, it is preferable that the dew-point temperature of the atmospheric gas throughout the whole area of the annealing furnace be controlled to be −50° C. or lower from the viewpoint of almost completely preventing the oxidation of Si and Mn. Incidentally, since, in the case where the dew-point temperature throughout the whole area of the annealing temperature is lower than −80° C., the equipment of a refiner becomes markedly large and there is a marked increase in running cost, the dew-point temperature is set to be −80° C. or higher.

Figure 4:
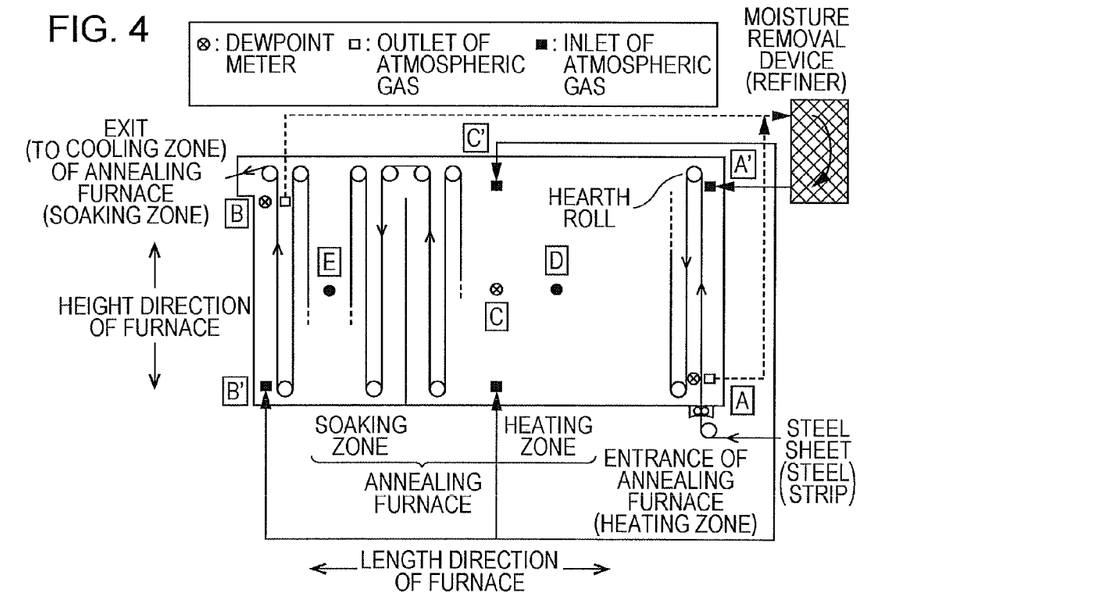
FIG. 4 is another schematic diagram illustrating an annealing furnace constituting the continuous galvanizing line according to an embodiment of the present invention.

In addition, although examples in which minimum necessary number of dew-point meters and outlets and inlets of the atmospheric gas is installed are shown in the description above, it is needless to say that these may be installed at positions other than the positions described above as illustrated in FIG. 4. However, in this case, it is necessary to prevent the gas from stagnating or being directly discharged in consideration of gas flow in the furnace. In addition, although FIGS. 2 through 4 illustrate examples of a vertical furnace to be used as an annealing furnace, the present invention may be applied to a transverse furnace (horizontal furnace).

EXAMPLES

By using a galvanizing line (comparative example) consisting of an annealing furnace illustrated in FIG. 2 which consists of dew-point meters placed at the central position of the heating zone and the soaking zone and in which the dew-point of the atmospheric gas in the furnace is controlled to be −40° C. or lower, and by using a galvanizing line (example of the present invention) consisting of an annealing furnace illustrated in FIG. 3 which consists of, in addition to the line illustrated in FIG. 2, dew-point meters with which the dew-point of the atmospheric gas is observed, outlets through which the atmospheric gas in the furnace is collected and inlets through which the atmospheric gas from which moisture has been removed with the moisture removal device described above is fed into the furnace, the dew-point meters and the outlets being placed at least at two points which respectively exist on the side wall in the vicinity of the entrance of the annealing furnace and on the side wall in the vicinity of the furnace top at the position where a steel sheet has a maximum end-point temperature, the inlets being placed at two points which respectively exist on the side walls on the sides opposite to the sides of the two points for the outlets in the height direction of the furnace, which further consists of a dew-point meter and an inlet, the dew-point meter being placed on the side wall at the central position in the height direction of the furnace of the position nearest to the entrance of the furnace in the length direction of the furnace within the area in which the temperature of the steel sheet becomes 600° C., the inlet being placed on the side wall in the vicinity (from 0.5 m to 5 m) of the furnace top at the position in the length direction of the furnace where the dew-point meter described above is placed and in which the dew-point of the atmospheric gas in the furnace is controlled to be −45° C. or lower, galvanized steel sheets were industrially manufactured, and the mean values and the variability (standard deviation) of the dew-point at the central position of the soaking zone of the annealing furnaces (point E in FIGS. 2 and 3) and the rate of occurrence of coating defects were investigated. Here, the coating defects described above refer to, for example, a decrease in adhesion between a steel sheet and a coated film and a condition in which the surface of a steel sheet is not coated with a coated film due to a decrease in wettability, and the rate of occurrence of the defects refers to a defect rate (%) which is defined as the ratio of the number of occurrence of the defects to the total number of the treated steel sheets.

TABLE 1

| No. | Hot Dip Galva- nizing Line | Target Upper Limit of Dew- point (° C.) | Observed Dew- point at Central Part of Soaking Zone (Point E) (° C.) | | Rate of Occurrence of Coating Defect (%) | Note |
|---|---|---|---|---|---|---|
| | | | Mean (° C.) | Standard Deviation (° C.) | | |
| 1 | FIG. 2 | −45 | −35 | 2.5 | 0.10 | Comparative Example |
| 2 | FIG. 3 | −45 | −47 | 1.8 | 0.01 | Example |
| 3 | FIG. 3 | −55 | −57 | 1.5 | 0.005 | Example |

Table 1 shows the results of the investigations described above, and it is clarified that, by using the galvanizing line according to the present invention, it is possible to steadily keep the dew-point in an annealing furnace to −45° C. or lower, which results in the rate of occurrence of coating defects being significantly decreased to one-tenth or less of that of a galvanizing line of the conventional methods.

The method according to the present invention can also be applied to a continuous annealing furnace for a cold steel sheet and a stainless steel sheet consisting of an annealing furnace.

The invention claimed is:

1. A continuous galvanizing line comprising:
an annealing furnace, heated solely by radiant tube heating, having an entrance where a steel sheet is conveyed into a heating zone, a soaking zone which receives the steel sheet after the heating zone, wherein said steel sheet reaches a maximum end-point temperature in the soaking zone, and an exit where said steel sheet leaves the annealing furnace, wherein said annealing furnace includes all radiant tube structure to provide heating, wherein said annealing furnace has a first side wall, a second side wall, a top, and a bottom, wherein said exit is located at the top or the bottom;
a plurality of outlets which collect an atmospheric gas in the furnace, wherein a first outlet is located on the first or second side wall in the vicinity of the entrance of the annealing furnace in the heating zone of the annealing furnace, and a second outlet is located on the first or second side wall in the vicinity of the furnace top or the furnace bottom at the position where the steel sheet has the maximum end-point temperature, said first outlet and said second outlet being located at opposite points in the height direction of the annealing furnace;
a moisture removal device which collects the atmospheric gas from the plurality of outlets and removes moisture from the atmospheric gas to provide an atmospheric gas having a dew point of −60° C. or lower;
a plurality of inlets which collect from the moisture removal device the atmospheric gas having a dew point of −60° C. or lower and feed the atmospheric gas having a dew point of −60° C. or lower into the annealing furnace, wherein said inlets are located at two points which respectively exist on the first or second side wall, a first inlet being located in the heating zone in the vicinity of the top of the furnace at a point opposite the first outlet with respect to the height direction of the annealing furnace, and a second inlet being located in the soaking zone in the vicinity of the bottom of the furnace at a point opposite the second outlet with respect to the height direction of the annealing furnace, wherein the plurality of inlets provide the atmospheric gas with a flow rate and dew-point and said plurality of inlets are configured to control the dew point of the atmospheric gas to be between −80° C. and −45° C. throughout the whole area of the inside of the annealing furnace; and
dew point meters, which measure the dew point of the atmospheric gas, wherein
a first dew point meter is located on the first or second side wall adjacent to the first outlet in the vicinity of the entrance of the furnace in the length direction of the furnace, and
a second dew point meter is located on the first or second side wall in the vicinity of the furnace top or the furnace bottom at the position where the steel sheet has the maximum end-point temperature.

2. The continuous galvanizing line according to claim 1, further comprising:
a third dew point meter located on the first or second side wall of the furnace in the heating zone at a position nearest the entrance of the furnace in the length direction thereof where the temperature of the steel sheet becomes 600° C.

3. The continuous galvanizing line according to claim 2, further comprising:
a third inlet, through which the atmospheric gas from which moisture has been removed with the moisture removal device is fed into the furnace, wherein said third inlet is located on the first or second side wall in the vicinity of the furnace top or the furnace bottom located at a same length position in the length direction of the annealing furnace as that of the third dew point meter.

4. The continuous galvanizing line according to claim 3, wherein the flow rate and/or the dew point of the atmospheric gas which is fed through each inlet can be separately adjusted in accordance with the dew point which is observed with the dew point meter nearest to the inlet.

5. The continuous galvanizing line according to claim 2, further comprising:
a third inlet, through which the atmospheric gas from which moisture has been removed with the moisture removal device is fed into the furnace, wherein said third inlet is located on the first or second side wall in the vicinity of the furnace top or the furnace bottom at a length position that is 0.5 m or more and 5 m or less from the third dew point meter in the length direction of the annealing furnace.

6. The continuous galvanizing line according to claim 3, wherein the dew point of the atmospheric gas is configured to be between −80° C. and −50° C. throughout the whole area of the inside of the annealing furnace.

7. The continuous galvanizing line according to claim 1, wherein the flow rate and/or the dew point of the atmospheric gas which is fed through each inlet can be separately adjusted in accordance with the dew point which is observed with the dew point meter nearest to the inlet.

8. The continuous galvanizing line according to claim 1, wherein the dew point of the atmospheric gas is configured to be between −80° C. and −50° C. throughout the whole area of the inside of the annealing furnace.

* * * * *

UNITED STATES PATENT AND TRADEMARK OFFICE
CERTIFICATE OF CORRECTION

PATENT NO. : 9,713,823 B2
APPLICATION NO. : 14/390648
DATED : July 25, 2017
INVENTOR(S) : Nobuyuki Sato It is certified that error appears in the above-identified patent and that said Letters Patent is hereby corrected as shown below:

In the Claims

At Column 10, Line 21, in Claim 1, "dew-point" should read --dew point--.

Signed and Sealed this
Fifth Day of September, 2017

Joseph Matal
*Performing the Functions and Duties of the*
*Under Secretary of Commerce for Intellectual Property and*
*Director of the United States Patent and Trademark Office*